(12) United States Patent
Chung et al.

(10) Patent No.: US 6,355,439 B1
(45) Date of Patent: Mar. 12, 2002

(54) METHOD FOR OBTAINING HUMAN SKIN DNA SAMPLES WITH AN ADHESIVE SHEET

(75) Inventors: Yeon Bo Chung, Seoul; Choon Hong Hwang, Kyunggi-do; Eun Young Kim, Seoul, all of (KR)

(73) Assignee: I.D. Gene, Inc. (KR)

( * ) Notice: Subject to any disclaimer, the term of this patent is extended or adjusted under 35 U.S.C. 154(b) by 0 days.

(21) Appl. No.: 09/787,794

(22) PCT Filed: Sep. 22, 1999

(86) PCT No.: PCT/KR99/00579

§ 371 Date: Mar. 23, 2001

§ 102(e) Date: Mar. 23, 2001

(87) PCT Pub. No.: WO00/17396

PCT Pub. Date: Mar. 30, 2000

(30) Foreign Application Priority Data

Sep. 23, 1998 (KR) .............................. 98/39409
Sep. 17, 1999 (KR) .............................. 99/40052

(51) Int. Cl.[7] .................................. C12Q 1/68
(52) U.S. Cl. ................ 435/6; 536/25.4; 536/25.41; 536/25.42; 428/41.4; 428/40.1; 428/41.7; 428/41.8; 428/351; 428/343
(58) Field of Search .............................. 435/6; 536/25.4, 536/25.41, 25.42; 428/41.4, 40.1, 41.7, 41.87, 351, 343

(56) References Cited

U.S. PATENT DOCUMENTS 4,524,104 A * 6/1985 Hagio et al. ................ 428/341
4,720,416 A * 1/1988 Duncan ...................... 428/195
5,211,286 A 5/1993 Turner
5,364,759 A 11/1994 Caskey et al.
5,856,102 A 1/1999 Bierke-Nelson et al.

OTHER PUBLICATIONS

Teimer, Gunter et al., "Isolation and Physicochemical Characterisation of the DNA from Normal Human Skin and Psoriatic Scales", *Arch Dem. Res.*, 1976, vol. 256, pp. 241–246.

Van Oorschot, Roland A.H. et al., "DNA Fingerprints From Fingerprints", *Nature*, Jum. 19, 1997, vol. 387, p.767.

Zamir, Ashira et al., "Fingerprints and DNA: STR Typing of DNA Extracted from Adhesive Tape after processing for Fingerprints", *Journal of Forensic Sciences*, May 2000, 45(3), pp. 687–688.

Y. B. Chung et al., "Palm Print on Stickers as a Replacement of Blood–drawing for DNA Tests", Proceedings of Tenth International Symposium on Human Identification—1999, sponsored by Promega Co., pp. 8pp. (http://www.promega.com/geneticproc/ussymp10proc/default.htm).

* cited by examiner

*Primary Examiner*—James Ketter
(74) *Attorney, Agent, or Firm*—Gates & Cooper LLP

(57) ABSTRACT

Provided is a method for obtaining human DNA for genetic analysis, by taking the epidermis of testee by means of an adhesive sheet, and by extracting DNA from the epidermis stuck on the adhesive sheet. Provided are also combined sheets for conveniently storing DNA and a kit for taking the epidermis and analyzing DNA. Along with the kits, the method allows DNA to be easily obtained and stably stored for a long period of time. In addition, both the identification and the DNA analysis of a testee can be conducted at the same time by taking epidermal scraps from the testee, along with a figured epidermal print.

19 Claims, 10 Drawing Sheets

1  2  3  4  5

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: 5' primer for the amplification of ACE gene

<400> SEQUENCE: 1
catcctttct cccatttctc                                                    20

<210> SEQ ID NO 2
<211> LENGTH: 22
<212> TYPE: DNA
<213> ORGANISM: Artificial Sequence
<220> FEATURE:
<223> OTHER INFORMATION: 3' primer for the amplification of ACE gene

<400> SEQUENCE: 2
atttcagagc tggaataaaa tt                                                 22

```
<210> SEQ ID NO 3
<211> LENGTH: 24
<212> TYPE: DNA
<213> ORGANISM: Artificial Sequence
<220> FEATURE:
<223> OTHER INFORMATION: 5' primer for the amplification of F13A01 STR
      sequence

<400> SEQUENCE: 3
gaggttgcac tcgagcctttt gcaa                                          24

<210> SEQ ID NO 4
<211> LENGTH: 24
<212> TYPE: DNA
<213> ORGANISM: Artificial Sequence
<220> FEATURE:
<223> OTHER INFORMATION: 3' primer for the amplification of F13A01 STR
      sequence

<400> SEQUENCE: 4
ttcctgaatc atcccagagc caca                                           24
```

METHOD FOR OBTAINING HUMAN SKIN DNA SAMPLES WITH AN ADHESIVE SHEET

This application was filed under 35 U.S.C. §371 as international application number PCT/KR99/00579 on Sep. 22, 1999, and claims benefit under 35 U.S.C. 517 119 of Korean patent application number 1998-39409, filed Sep. 23, 1998, and number 1999-40052, filed Sep. 19, 1999.

TECHNICAL FIELD

The present invention relates, in general, to a method for obtaining DNA samples using an adhesive sheet and, more particularly, to a method for obtaining DNA samples from human epidermal scraps which are taken with the aid of an adhesive sheet. Also, the present invention is concerned with combined sheets for storing DNA and with a kit for obtaining DNA from the epidermal scraps.

PRIOR ART

The genetic material DNA (deoxyribonucleic acid) constitutes the genes encoding the synthesis of cellular components and metabolisms of all creatures. The great advances of life science in the latter half of the 20th century, including the Genome Project, predicts the generalization of genetic analysis.

As a consequence of the Genome Project, human beings are able to read all of the genetic information of human DNA and the genes responsible for or involved in hereditary diseases have been discovered one after another. In addition, genetic abnormalities are now comprehended in a nucleotide sequence level. Accordingly, knowledge of gene types involved in diseases will allow potential patients to take appropriate precaution as well as enable doctors to give appropriate prescription and treatment.

Since DNA is ubiquitous in every cell and DNA type is discriminable between individuals, there have been developed genetic identification (or DNA profiling) methods which can discern individuals from one to another at a gene level. By virtue of its accuracy, the genetic identification technique is regarded as the best tool in fields such as forensic tests and paternity tests. In practice, in the U.K. and the U.S., DNA profile databases for prisoners have been constructed and used to examine suspects with the aid of computers by comparing DNA profiles obtained from evidences obtained from the scenes of crimes.

Whether it is used for disease diagnosis or genetic identification, DNA is usually obtained from blood. Blood sampling for DNA profile, however, is problematic for the following reasons:

First, blood sampling should be conducted by specialized workers, such as doctors or nurses.

Second, testees suffer discomfort upon the blood sampling.

Third, there always exists the possibility of blood handlers being infected with diseases, such as hepatitis or AIDS.

Fourth, blood sampling may be unobtainable on account of age, health, religion, etc.

Fifth, blood sampling is associated with cumbersome problems. In this regard, because direct identification of testees is impossible only by blood samples taken from testees, their photographs and fingerprints should be taken to assure the reliable match of blood donors with testee, and relevant samplers, carriers, and analyzers make out the chain of custody documents. For example, the FBI of the U.S.A. has established a guideline such that anyone and all who are involved anywhere in the chain of custody sign or otherwise witness such involvement including those carrying and handling blood samples. Assurance is made double in marking blood samples (Technical Working Group on DNA Analysis Methods, "Guidelines for a quality assurance program for DNA analysis" Crime Laboratory Digest, 22:21–43, 1995).

Sixth, compulsory blood sampling for executing laws is adjudged to be against the Constitution in the U.S.A. (Lehrman, Nature 394:818, 1998).

In order to overcome such inconveniences, an attempt has recently been made to use mouth epithelial cells instead of blood. The mouth epithelial cells have advantages over blood samples in various aspects. However, similar complicated procedures, documents and witnesses as in the case of blood sampling are needed in order to assure the reliable match of a sample donor with a particular testee. In addition, the sampling of epithelial cells within the body causes the testee to show reluctance to it.

DISCLOSURE OF THE INVENTION

The intensive and thorough research on genetic identification, repeated by the present inventors aiming to overcome the conventional problems occurring upon the sampling of blood or oral cells, resulted in the finding that the epidermis could be an ideal source for DNA and that DNA materials could be obtained from epidermis at a sufficiently large amount for DNA analysis by use of an adhesive sheet with an advantage of not taking other separate identification measures. That is, when DNA is obtained from the epidermis of the fingers, the palms, the foot soles or the toes by use of adhesive sheets, sufficient amounts of DNA are reserved on the adhesive sheets, together with fingerprints, palm prints, footprints or toe prints, which allow the donors of DNA samples to be always discerned individually without taking photographs and utilizing other identification procedures. Since the epidermal scraps attached on the adhesive sheet of the present invention are in a dry state, the DNA in the scraps can be stably conserved for a long period. Together with the prints printed on the adhesive sheet, DNA profiles which are obtained from the epidermis attached to the sheet can be used for the identification of unknown corpse, paternity test, investigation on hereditary diseases, etc.

Therefore, it is an object of the present invention to overcome the above problems encountered in prior arts and to provide a method for obtaining DNA, by which both DNA sampling and the identification of a testee can be performed simultaneously.

It is another object of the present invention to provide a means for obtaining or storing DNA samples from individuals or a population.

In one aspect of the present invention, there is provided a method for obtaining human DNA by taking the epidermis of a testee by means of an adhesive sheet and by extracting DNA from the epidermis stuck on the adhesive sheet.

In another aspect of the present invention, there is provided a method for genetic analysis using human DNA, comprising the steps of taking epidermal scraps from the skin of a testee by use of an adhesive sheet; visualizing the epidermal print as an image; recording the image in an optical or electronic medium; extracting DNA from the epidermal scraps stuck on the adhesive sheet; and measuring physical and chemical properties of the DNA.

In a further aspect of the present invention, there is provided combined sheets for taking the epidermis or for storing DNA, comprising an adhesive sheet and a protective sheet for protecting an adhesive surface of the adhesive sheet.

In still a further aspect, there is provided a kit for taking epidermal scraps or for extracting DNA, comprising the combined sheets for taking the epidermis or for storing DNA.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE PREFERRED EMBODIMENTS

In the present invention, DNA can be secured from the epidermis. In this regard, an adhesive sheet is utilized to obtain epidermal scraps which are sources for DNA. That is, DNA is extracted from the epidermal scraps stuck on the adhesive sheet.

Therefore, in one aspect, the present invention provides a method for obtaining DNA from the epidermis by use of an adhesive sheet.

The term "epidermis or epidermal scraps" as used herein means tissues existing on the surface of human or animal skin or materials secreted therefrom, which are used as a DNA source from which DNA can be extracted, in the present invention.

Figure 1:
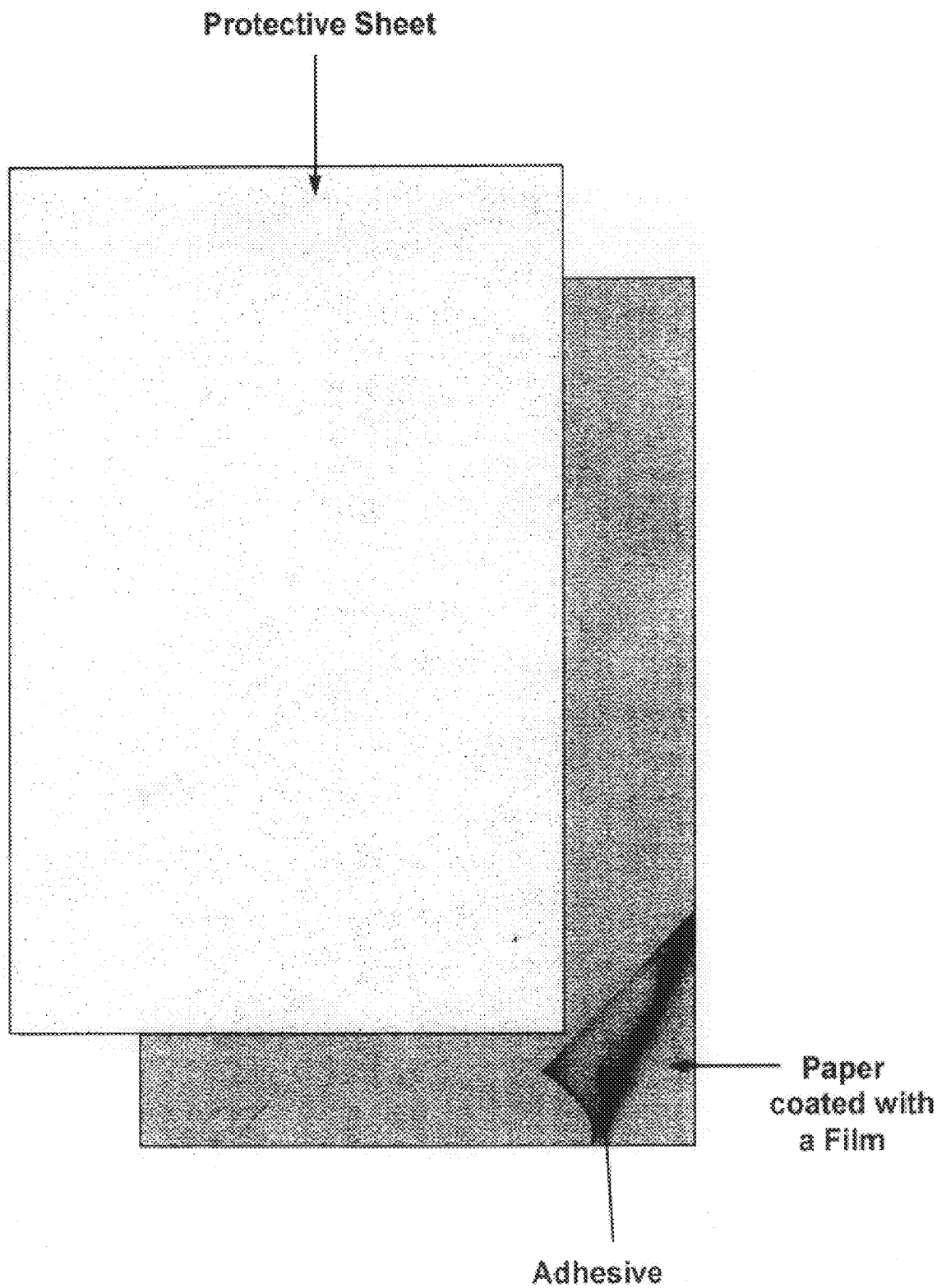
FIG. 1 shows a structure of an adhesive sheet for taking the epidermis, in accordance with the present invention.

The term "adhesive sheet" as used herein means a sheet-like structure in which an adhesive agent is applied on at least one surface of a support. An adhesive sheet useful in the present invention is composed basically of a support and an adhesive applied thereon, as shown in FIG. 1. The support is made of a solid material which can be formed into a sheet-like form and applied with an adhesive. Examples of the support materials available in the present invention include paper; synthetic resins, such as cellulose, polypropylene, polyethylene and PVC; fibers, such as those used in adhesive plasters; and metals such as aluminum.

Fundamentally, the adhesive sheet is prepared by applying an adhesive on one side of a support. Optionally, the opposite sides of a support may be applied with an adhesive while one of the opposite sides is backed by, for example, an unfoldable plastic plate.

Where the support is made of paper, its opposite sides are preferably coated with a insoluble film because various inhibitory materials are released from paper upon DNA extraction.

Figure 7:
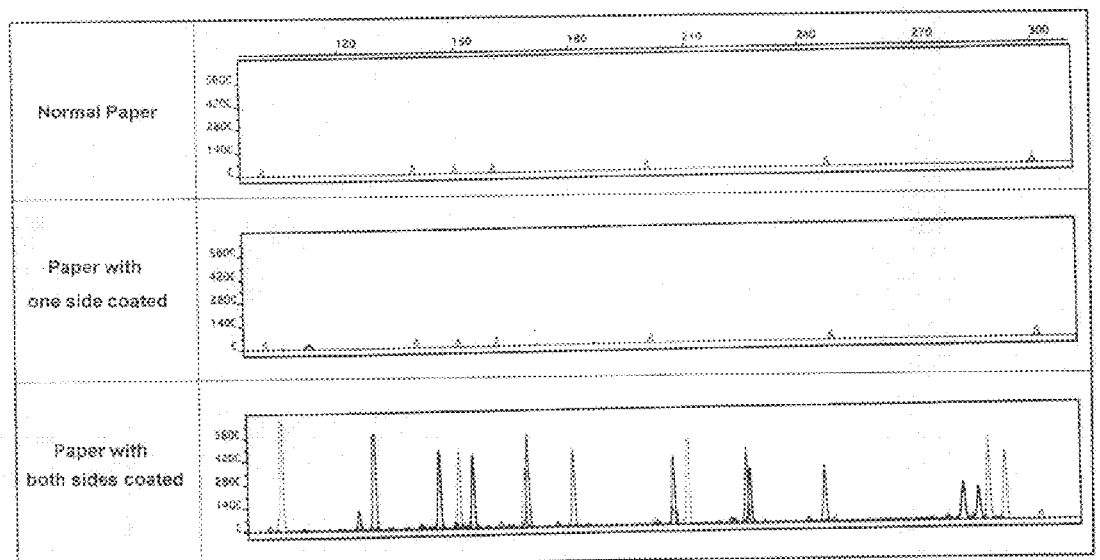
FIG. 7 shows electropherograms which illustrate that DNA analysis is impossible when the epidermis is taken by non-adhesive paper or by an adhesive sheet with only one side coated with film.

The adhesive and the coatings play a very important role in taking DNA from the epidermis (see FIG. 7). When the epidermis is taken by use of adhesive-lacking paper, it is virtually impossible to detect DNA even after polymerase chain reaction (PCR) amplification with fluorescent- or radio-labeled primers. It is believed that uncoated or one-side-coated adhesive sheets take epidermal scraps to the same degree as in a both-sides-coated adhesive sheet, but inhibitory materials against DNA extraction are released from the uncoated or one-side-coated sheets, making it impossible to read DNA peaks upon primary PCR. In this case, re-amplification of the primary PCR product may allow DNA detection, but it is not recommended because of complication in procedure, economical unfavorableness, and high error rates.

It is preferred that a coated protective sheet which does not react with the adhesive is covered over the adhesive surface in order to protect the adhesive surface and the epidermal scraps attached thereto, as shown in FIG. 1.

The adhesive sheet of the present invention is made into an enough large size to take in the hand or the foot, for example a A5 or B5 size. If necessary for storage, carriage and other reasons, the adhesive sheet may be reduced to a size apt to accommodate only fingers or toes.

It is preferred that epidermal scraps are obtained from the palms, the fingers, the sole of the foot, and/or the toes. The prints from these body sites allow the donors of the epidermis to be identified (see FIGS. 2 and 3).

It is most preferable to secure epidermal scraps from the palm. In the case that the palm is not clearly printed as in new-born babies, epidermal samples may be obtained by attaching the adhesive sheet on other skin surfaces, such as the sole of the foot, the chest, etc. The skin surfaces to be printed on the adhesive sheet of the present invention must be clean and dry lest the epidermis sampling should be hindered by a film which is formed between the skin surfaces and the adhesive by powders, water, oils and the like stained on the surfaces.

The epidermis left on the adhesive sheet is used for DNA extraction. Although various known methods for DNA extraction are available, the following method is preferable in DNA extraction from the epidermis attached to the adhesive sheets: the sheet containing the epidermis is entirely or partially immersed in an extraction buffer which is then boiled, followed by alcohol precipitation of DNA. The DNA extraction buffer comprises mixed ion-exchange resins and proteases. Exemplified by Chelex-100 (Bio-Rad, U.S.A.) and Amberlite IRN-150 (Supelco, U.S.A.), the mixed ion-exchange resins useful in the present invention comprise both cationic and anionic components. Any of the non-specific proteases, including Protease K, which are commonly used for DNA isolation may be employed in the present invention.

In detail, a piece (1.5 cm×0.5 cm) of an adhesive sheet containing epidermis is placed in a test tube containing the DNA extraction buffer. Alternatively, a cotton stick soaked in a 0.2 N NaOH solution may be used to scrape the epidermis on the adhesive sheet. In this case, the collected epidermis is then added in the extraction buffer.

Figure 4:
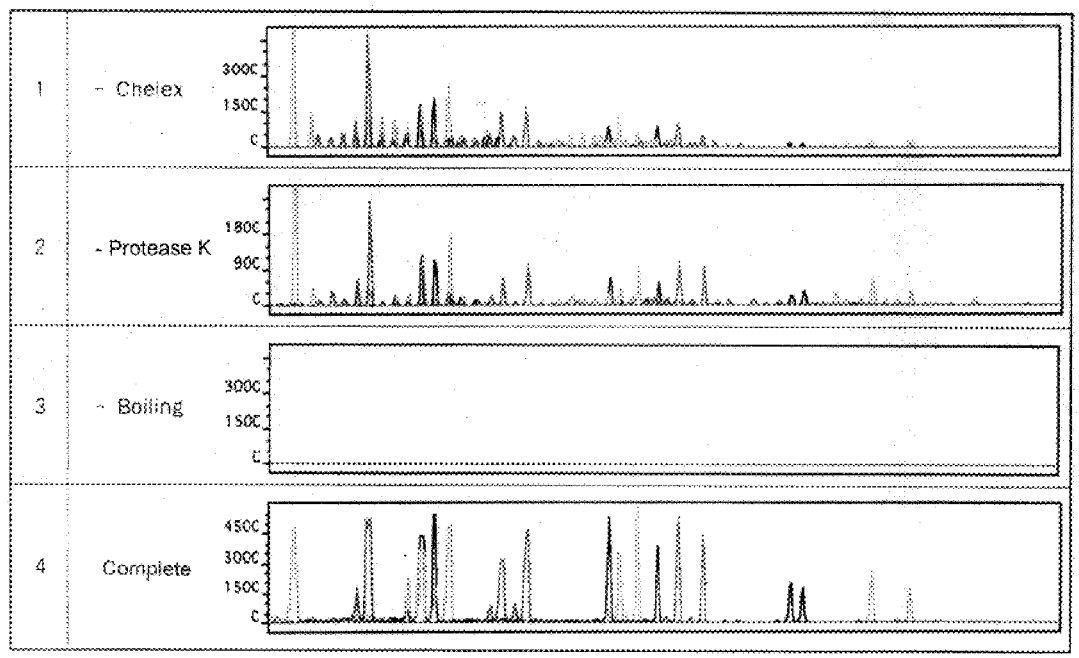
FIG. 4 shows electropherograms which illustrate the influence of the various factors used for DNA isolation on the DNA analysis.

In one Example of this invention, the inhibitors of PCR are removed by the actions of ion-exchange resin (for example, Chelex-100) and protease in the extraction buffer. When the epidermis is not treated with the ion-exchange resin or the protease, many non-specific peaks appear, interrupting accurate reading of accurate peaks as measured by electropherogram (see FIG. 4). The subsequent boiling step is the most efficient and direct means in extracting DNA by releasing the epidermis from the adhesive sheet into the solution phase, as shown in FIG. 4. No DNA is obtained without a boiling step. Through alcohol precipitation, the DNA is recovered as pellets. After being dried, the pellets are dissolved in a suitable volume of a buffer. The DNA obtained, if necessary, may be amplified by PCR.

Figure 5:
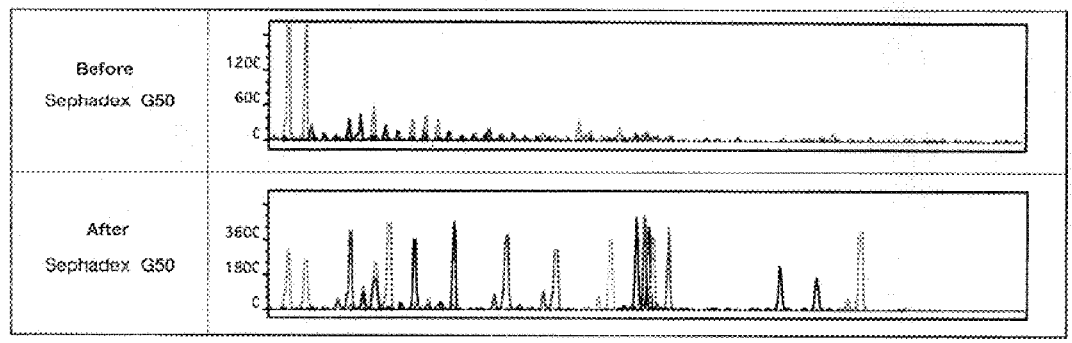
FIG. 5 shows electropherograms which illustrate the effect of additional purification by Sephadex G-50 chromatography on the removal of inhibitory materials.

In most cases, the above procedure produces purified DNA with an amount sufficient for the subsequent genetic analysis. However, the inhibitory materials may be insufficiently removed, according to personal traits: skin types and epidermal states upon sampling. In this case, an additional purification process is necessary. Preferable is a chromatographic process which can exclude materials with molecular weights of as low as several tens of thousands. For instance, impurities which are as low as tens of thousands in molecular weight can be efficiently removed by use of a molecular sieving chromatographic resin such as Sephadex G-50 (Sigma, U.S.A.) and a filter such as Microcon 100 (Amicon, U.S.A.). Following this additional purification, more purified DNA and more clear PCR results can be obtained, as shown in FIG. 5.

Figure 6:
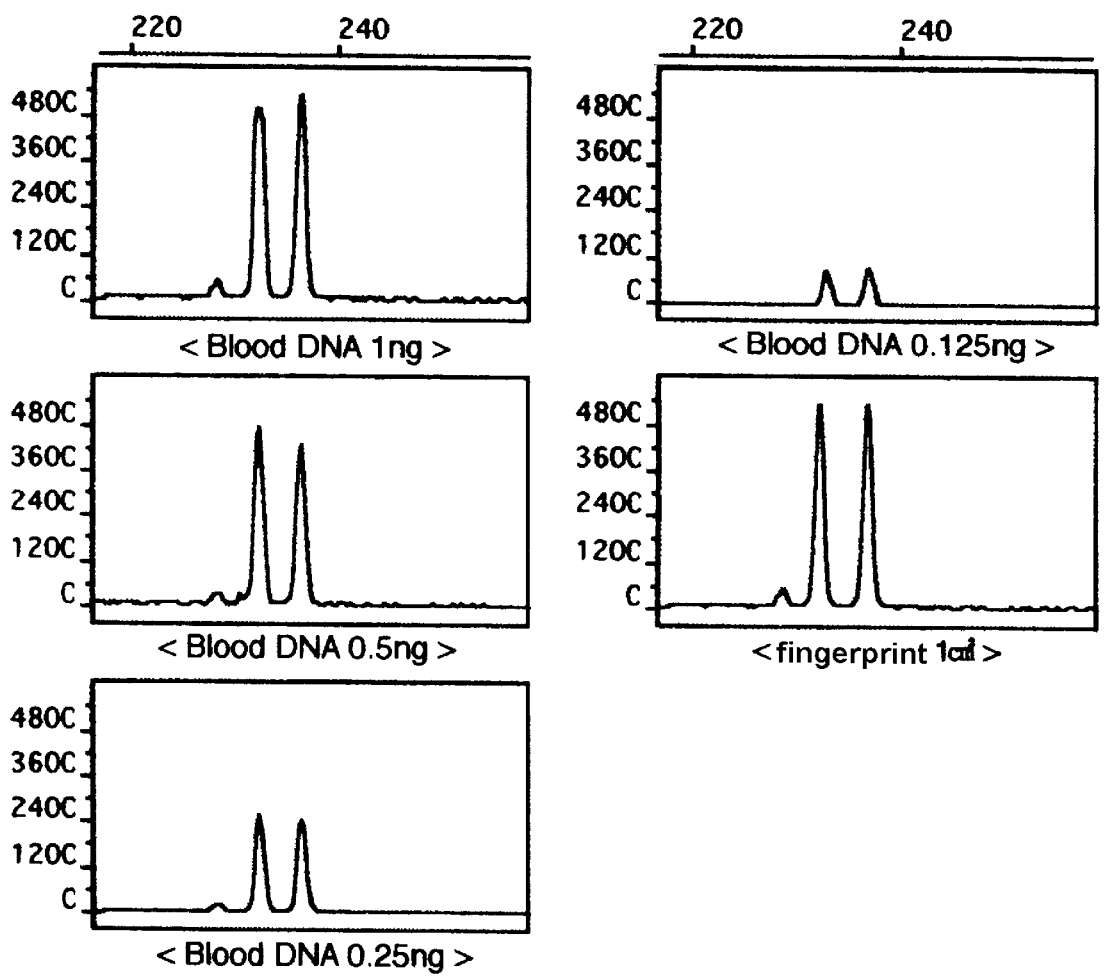
FIG. 6 shows indirect quantification of the epidermal DNA extracted from a 1.5 cm×0.5 cm piece of the adhesive sheet.

As for the amount of the DNA obtained from the adhesive sheet, it is very small so that accurate measurement is not easy, but it can be indirectly measured. For example, when being accurately measured, the DNA extracted from bloods can be diluted into a concentration range similar to that of the DNA extracted from the adhesive sheet. When DNA is amplified by PCR, the amplification is proportional to the copy number of the DNA template used until it reaches to completely saturated state. Therefore, an indirect estimation for the quantity of the DNA obtained from the adhesive sheet can be achieved by amplifying the DNA, along with a diluted control DNA sample, under a condition. Through this indirect measurement, it was found that about 1 ng of epidermal DNA could be obtained from an area of 1.5 cm×0.5 cm of the adhesive sheet (see FIG. 6).

In another aspect, the present invention provides a method for analyzing human genes, in which the epidermal scraps are obtained by use of an adhesive sheet and DNA is isolated from the epidermal scraps and measured for physicochemical properties. The method for genetic analysis comprises the following steps:

a) taking epidermal scraps from a testee by use of an adhesive sheet;

b) visualizing the epidermal print to an image;

c) recording the image in an optical or electronic medium;

d) isolating DNA from the epidermal scraps stuck on the adhesive sheet; and e) identifying physical and chemical properties of the DNA.

The steps a) and d) can be implemented by the method for obtaining DNA previously described.

Where the palm or the foot sole is imprinted on the adhesive sheet, the palm print, finger print, or toe print figured on the adhesive sheet can be visualized by suitable dye. Preferable as a dye is crystal violet. After the palm or foot sole is impressed on the adhesive sheet, a reflection of the shallow wrinkles of the epidermis is printed on the adhesive sheet. By immersing the sheet in 1% crystal violet solution for about 10 sec and washing the sheet with distilled water, an image of palm-print or footprint appears clear blue (see FIGS. 2 and 3).

As a rule, the quantity of DNA obtainable from the adhesive sheet is proportional to the intensity of the crystal violet dye stained on the adhesive sheet. As for a palm print, the central portion of the palm is little printed, while a lower portion of the palm is well stained. The intensity of staining also depends on the personal skin type, driness of hand upon sampling and so on. A piece of the printed sheet, with a size of 1.5 cm×0.5 cm, corresponding to the well-dyed portion, allows the production of DNA at an amount of as much as 1 ng (see FIG. 6). This size fits a 1.5-ml microtube.

In respect to the recording and storing of the epidermal image visualized by dye, there is needed an optical or electronic instrument. For example, because the palm print or fingerprint has very fine patterns, they are difficult to discern with the naked eye. A magnifying glass may be employed for the close observation of the image, and a close-up lens is useful for taking a photograph of the image. An image photographed on a film by an analog camera can be computerized into a digital file through a scanner. Alternatively, the palm print or fingerprint can be directly input as a computer file by taking advantage of a digital camera or scanner. The sameness between two or more palm prints, fingerprints, or footprints can be determined with the aid of a magnifying glass or a conventional computer software. These computerized images for fingerprints, palm prints, and footprints of testee may be recorded and stored in conjunction with the analysis results obtained in the step e).

As for the identification of the physical and chemical properties of the DNA, it can be achieved either by examining the physicochemical properties of nucleotide sequence such as the length of DNA fragments amplified by PCR, the hybridization behaviors, the electrophoretic mobility, etc, or by direct sequencing the DNA. The examinations where the hybridization behaviors are investigated include conventional Southern blot analysis, automated analysis using DNA chips, and so on. In addition, the examinations where the electrophoretic mobilities include SSNP, SSCP assay and the like.

The object of DNA analysis determines which type of the examination may be employed. If the DNA analysis aims at DNA typing such as paternity test or forensic test, DNA samples will be used for the determination of the type of a specified gene. In this regard, the genes or gene segments of interest are selected depending on the final object of the DNA analysis. For instance, when the object is the genetic identification for individuals associated with paternity test or forensic test, the target will be directed to several STR (Short Tandem Repeat) loci. When the interest focus on a particular disease or research on a particular gene itself is purposed, the target will be one or several genes of the human genes which is estimated to be eighty thousands. Amplified are some of the nucleotide sequences of the target genes.

To measure the physicochemical properties of DNA, conventional labeling procedures may be employed, wherein the target gene or its complementary nucleotide sequence is labeled for the quantitative or qualitative analysis. Preferable labeling procedures include autoradiography, fluorescence labeling, and so on. Alternatively, silver staining may be used for the detection of non-labeled DNA.

Genetic analysis of the Step e) is divided largely into two categories.

Figure 8:
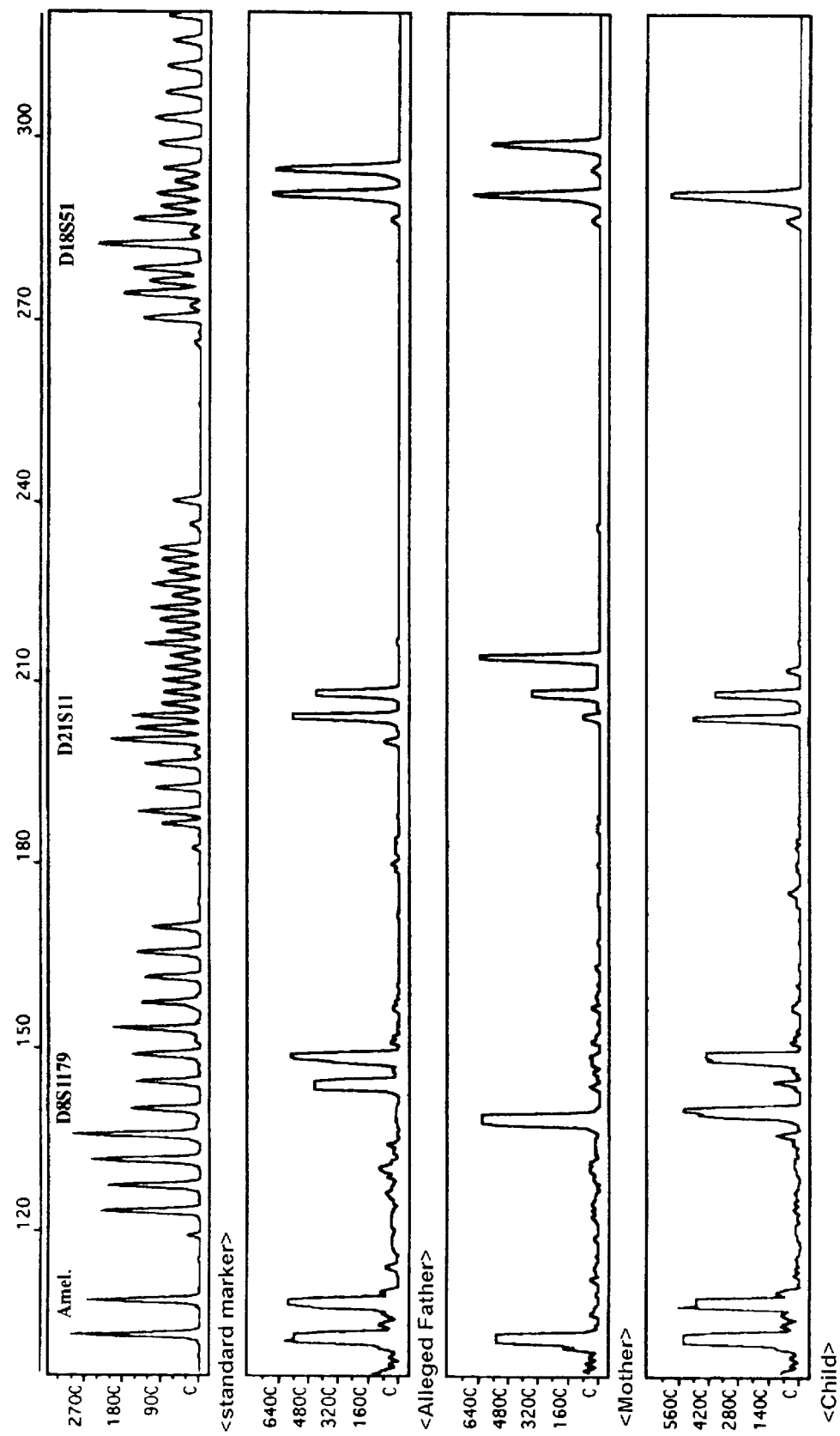
FIG. 8 shows allele characteristics in three STRs and an amelogenin gene as a result of paternity test, where nine STRs (short tandem repeats) and the amelogenin gene are amplified through multiplex PCR wherein the DNA isolated from the adhesive sheet are employed as a template.

Discrimination of alleles is subject to one of the two. For instance, different types of the STRs are presumptively determined by the sizes of the amplified DNA fragments. In one Example of the present invention, STRs and amelogenin gene were investigated in terms of the length difference in the genes by use of a DNA profiler kit. In another example, the profiler kit is practically applied for the paternity test. When DNAs isolated from the epidermal scraps stuck on adhesive sheets are amplified by PCR, the STR alleles which are in common between a real child and its parents are apparently detected, as shown in FIG. 8.

The other type of genetic analysis is to determine the nucleotide sequence of a gene. Since a difference in length between DNA fragments is, in consequence, due to an insertion or deletion of nucleotides, the determination of nucleotide sequences is accompanied by the discrimination of length differences. In addition, the determination of nucleotide sequences provides information concerning mutations which have absolute influence on the physiology of the organism but give no difference in DNA fragment length. These mutations include transposition or inversion and are difficult to detect by other techniques than direct sequencing.

In the present invention, F13A01 (one of STR locus) and the partial ACE (angiotensinogen converting enzyme) gene were amplified for sequencing. Like other genes related to cancers or hereditary diseases, the ACE gene and the F13A01 STR are unique genes in the whole genome, so-called single-copy genes. This demonstrates that even a single-copy gene can be detected and reasonably sequenced when DNA is obtained from the adhesive sheet and amplified.

Figure 9A:
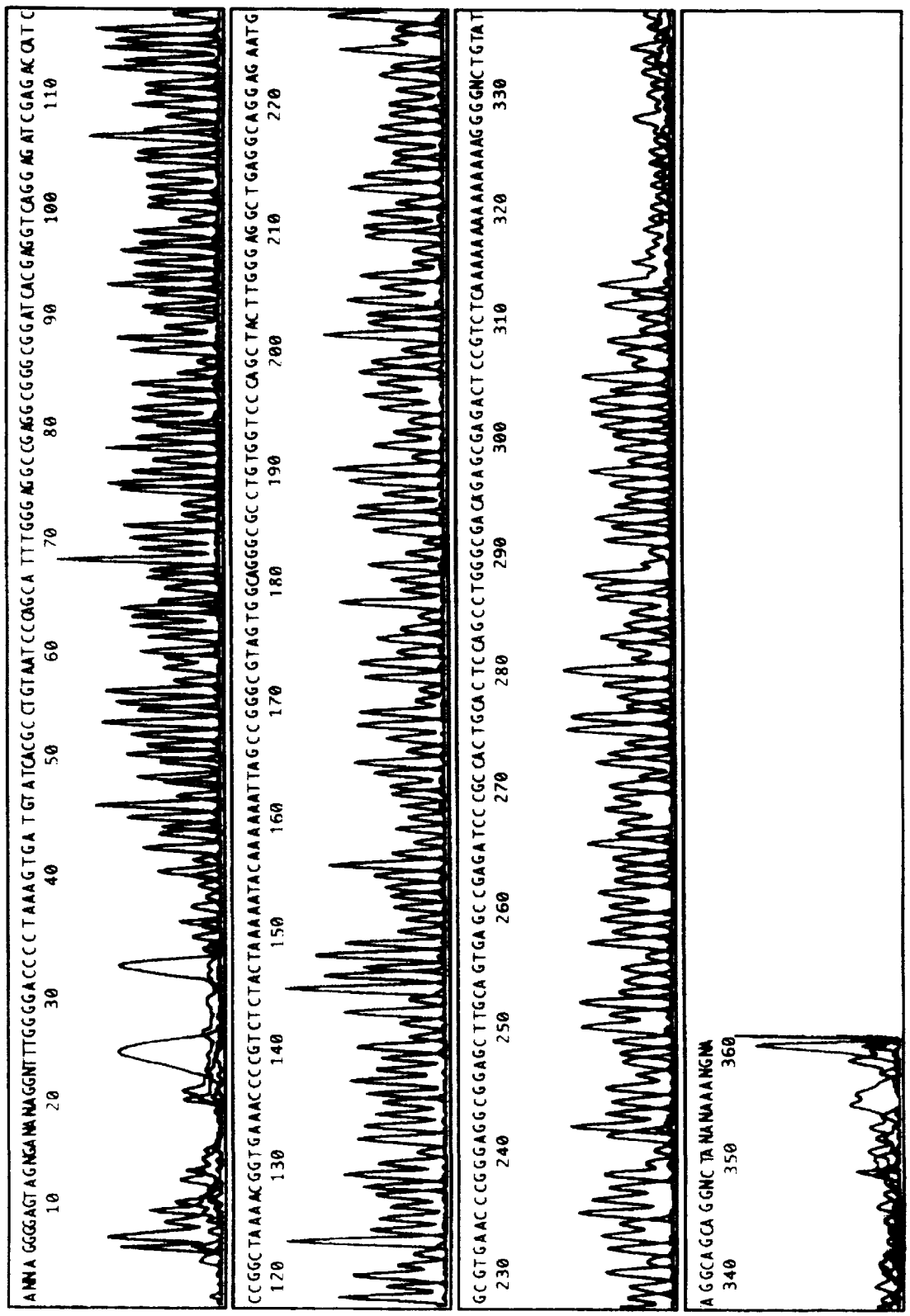
FIG. 9a shows a nucleotide sequence of an ACE (angiotensinogen converting enzyme) gene, which is obtained using the DNA isolated from blood.
Figure 9B:
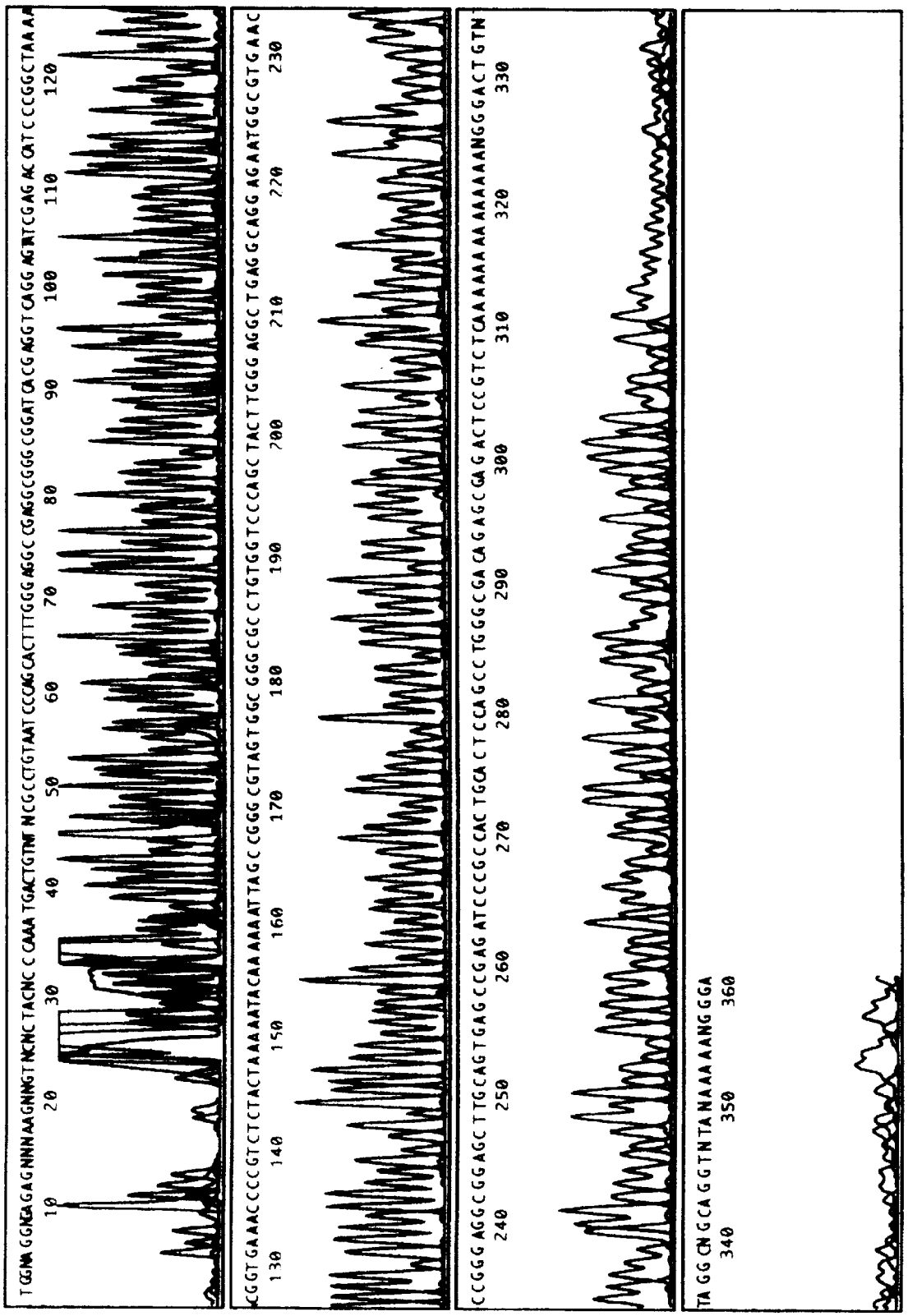
FIG. 9b shows a nucleotide sequence of the same ACE gene which results from the sequencing of the DNA obtained by use of the adhesive sheet of the present invention.
Figure 9C:
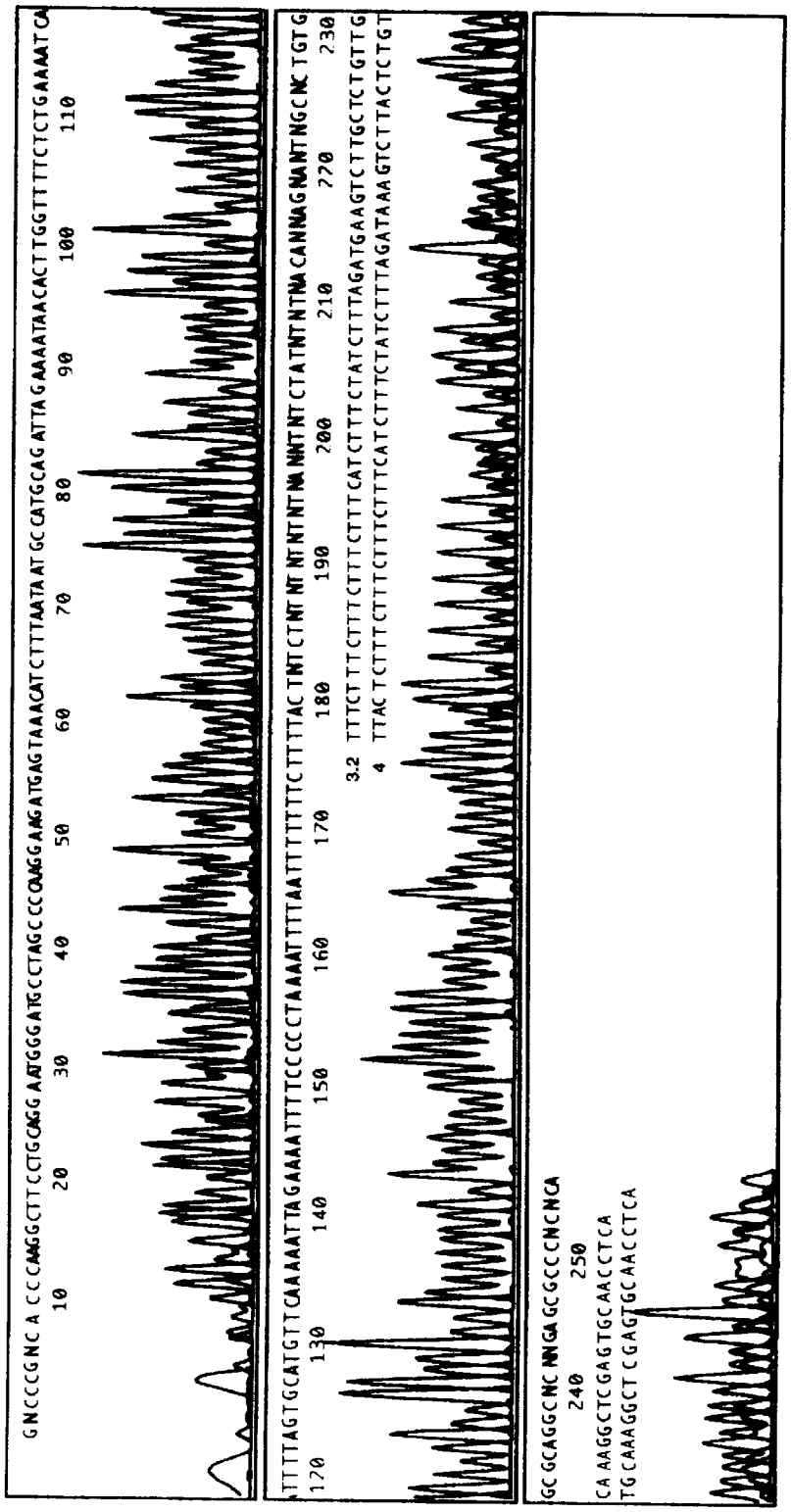
FIG. 9c shows a nucleotide sequence of an F13A01 region, which is determined using the DNA obtained by use of the adhesive sheet.

With reference to FIG. 9, there are results of DNA sequencing in an automatic sequencer. FIG. 9a is a nucleotide sequence of ACE gene, which is obtained using 5 ng of DNA isolated from blood, while FIG. 9b is a nucleotide sequence of the same region which results from the sequencing of the DNA obtained by use of the adhesive sheet of the present invention. FIG. 9c is a nucleotide sequence of an F13A01 region, which is determined using the DNA obtained by use of the adhesive sheet. Particularly, since the F13A01 gene has alleles 3.2 and 4, a genomic DNA, which is extracted from a heterozygote, is selected for the determination of their nucleotide sequences. This result comes from the coexistence of different nucleotide sequences in a portion of two amplified DNA fragments, demonstrating that the DNA obtained from the adhesive sheet of the present invention can be useful for research on SNP (single-nucleotide polymorphism) or in analyzing the mutation of nucleotide sequences.

In Examples corresponding to FIG. 4 to 8, it is determined whether the DNA extracted from the adhesive sheet is suitable for genetic identification. Particularly, a DNA profiler kit (Profiler-Plus, Perkin Elmer, U.S.A.) which was developed for genetic identification is used for PCR, and subsequent examination by use of ABI310 automatic nucleotide sequencer (Perkin Elmer, U.S.A.) was performed to determine the patterns of alleles.

The Profiler-Plus kit was developed to simultaneously amplify 10 gene regions, including 9 STR regions and an amelogenin gene, whose differences in the nucleotide sequences of X and Y chromosomes are utilized for sex discrimination. This simultaneous amplification of multiple genes is more difficult to achieve than amplification of one or two nucleotide sequences in other tests. Thus, if the PCR products of the ten regions of the Profiler-Plus kit and their electrophoretic patterns are obtained apparently, this confirms that the DNA sample can be used in all general PCR and electrophoresis. The Profiler-Plus kit contains the nine pairs of STR primers, and only 5'-end primer of each pair is labeled with a fluorescent dye. Three STRs in which the fragment size ranges of alleles are not overlapped are subject to one group, and the groups are discriminated from one another by use of three different colors of fluorescent dyes. When they are electrophoresed in an automatic nucleotide sequencer, the mobility of DNA fragments is determined from the period of time which it takes for them to reach a point irradiated with a laser beam while the bands shown in conventional electrophoresis appear as peaks on the X axis in Figures. In this electropherogram, its left end is the position of the laser source, corresponding to the bottom end in a conventional gel, and larger fragments are in farther right positions. Reflecting the intensity of fluorescence, the height of peaks is proportional to DNA quantity. The three different fluorescent markers are separately recognized and shown as three different colors.

If the DNA obtained from the adhesive sheet is sufficiently purified and is plentiful enough to be detected by such a fluorescent-labeling system, clear peaks are read at the positions of each allele of STR and amelogenin on an electropherogram: otherwise, no peaks are detected, there appear peaks which are too low to be discerned from the background, or non-specific peaks which are too different to secure reliability.

In a further aspect, the present invention provides combined sheets which is used to take the epidermis from individuals and to store the DNA of the epidermis donors. This combined sheets for taking the epidermis or for storing DNA comprises an adhesive sheet for taking the epidermis and a protective sheet.

The adhesive sheet for taking the epidermis is identical, in structure, to the adhesive sheet used in the step a) of the method for obtaining epidermal DNA. That is, the adhesive sheet for taking the epidermis comprises a support whose one side is applied with an adhesive. Made of paper, synthetic resin, fiber and metal, the support is prepared by coating an insoluble film on at least one side thereof.

The protective sheet may be made of any flexible material which is not stuck to the adhesive surface. Not preferable is a material reactive with the adhesive surface or the epidermal scrap attached thereto. Preferable materials for the protective sheet are exampled by a paper whose one side is coated with insoluble film.

The combined sheets for taking the epidermis or for storing DNA may be used as a mean to store epidermal samples of an individual or a population, or as a mean to carry DNA to an institute of genetic analysis.

In still another aspect, the present invention provides a kit for taking the epidermis or for extracting DNA, the kit containing one or more combined sheets for taking the epidermis or for storing DNA.

The uses of the kit include sampling the epidermis from one or more testee, reserving the epidermis for future use, obtaining the epidermis in order to extract DNA, and so on.

The fundamental component of the kit is the combined sheets for taking the epidermis or for storing DNA, whose characteristics are disclosed earlier.

Additional components of the kit may include crystal violet solution; mixed ion-exchange resins; proteases and buffer thereof; sodium acetate, potassium acetate or sodium chloride solution; TE buffer or Tris buffer; columns for molecular sieving chromatography; filter; users' manual; and so on.

Of the additional components, the crystal violet solution is employed for the staining of palm-print, fingerprint and the like, preferably provided with 1% (w/v) concentration.

The mixed ion-exchange resins; the proteases and buffer thereof; the sodium acetate, the potassium acetate or the sodium chloride solution; and the TE buffer or the Tris buffer are DNA extraction agents from the epidermis. The mixed ion-exchange resins are exampled by Chelex-100 (Bio-Rad, U.S.A.) and Amberlite IRN-150 (Supelco, U.S.A.). The proteases are represented by Protease K, and the protease buffer preferably contains 50 mM Tris (pH 7.5) and 5 mM sodium chloride. The sodium acetate, potassium acetate and sodium chloride solution, the salts used in conventional alcohol precipitation, may be preferably provided with 0.3 M concentration. In addition, diluted alcohol (preferably 95% and 70%) may be included in the kit of the present invention. The TE buffer (10 mM Tris, 1 mM EDTA, pH 8.0) or Tris buffer is employed for resuspending DNA pellet or for preserving DNA for long term, Tris buffer preferably being prepared with 10 mM concentration and adjusted to pH 8.0.

The columns for molecular sieving chromatography and the filter are useful for an additional purification in case of the insufficient elimination of the inhibitors of subsequent reaction. Preferable are column or filter which can exclude molecules with molecular weight less than tens of thousand kDa. The resins for the column is best exampled by Sephadex G-50 (Sigma, U.S.A.), while the filter by Microcon 100 (Amicon, U.S.A.).

Additionally, the kit may contain 1.5-ml microtubes as an instrument for DNA extraction.

The kit may further comprise a series of reagents for PCP, for example, a PCR buffer, nucleotides, a heat-resistant species of DNA polymerase, and primers. The region to be amplified with the aid of the primers, is determined depending on the final aim of DNA analysis. For instance, amplification may be allowed to occur on the entire region or a partial region of one or more genes for disease diagnosis or genetic research. Amplified gene in case of genetic identification may be one or more STRs and/or a portion of a target gene such as amelogenin.

A better understanding of the present invention may be obtained in light of the following examples which are set forth to illustrate, but are not to be construed to limit the present invention.

EXAMPLE I

Adhesive Sheet for Taking the Epidermis

Preferred embodiment of the adhesive sheet used in the method for isolating DNA from the epidermis is illustrated in FIG. 1. The adhesive sheet shown in FIG. 1 comprises an adhesive which will be brought into contact with the skin, and a support which is made of paper and applied with the adhesive. Further, in order to protect the adhesive and epidermal scraps stuck on the adhesive from contamination or loss, a coated protective sheet which cannot interact with the adhesive is used. Where the support is paper as in FIG. 1, it is necessary to coat the both sides of the support in order to prevent inhibitory materials from being released from the paper during DNA extraction. The coating effect will be described later (Example VII).

EXAMPLE II

Stained Palm Print

Figure 2:
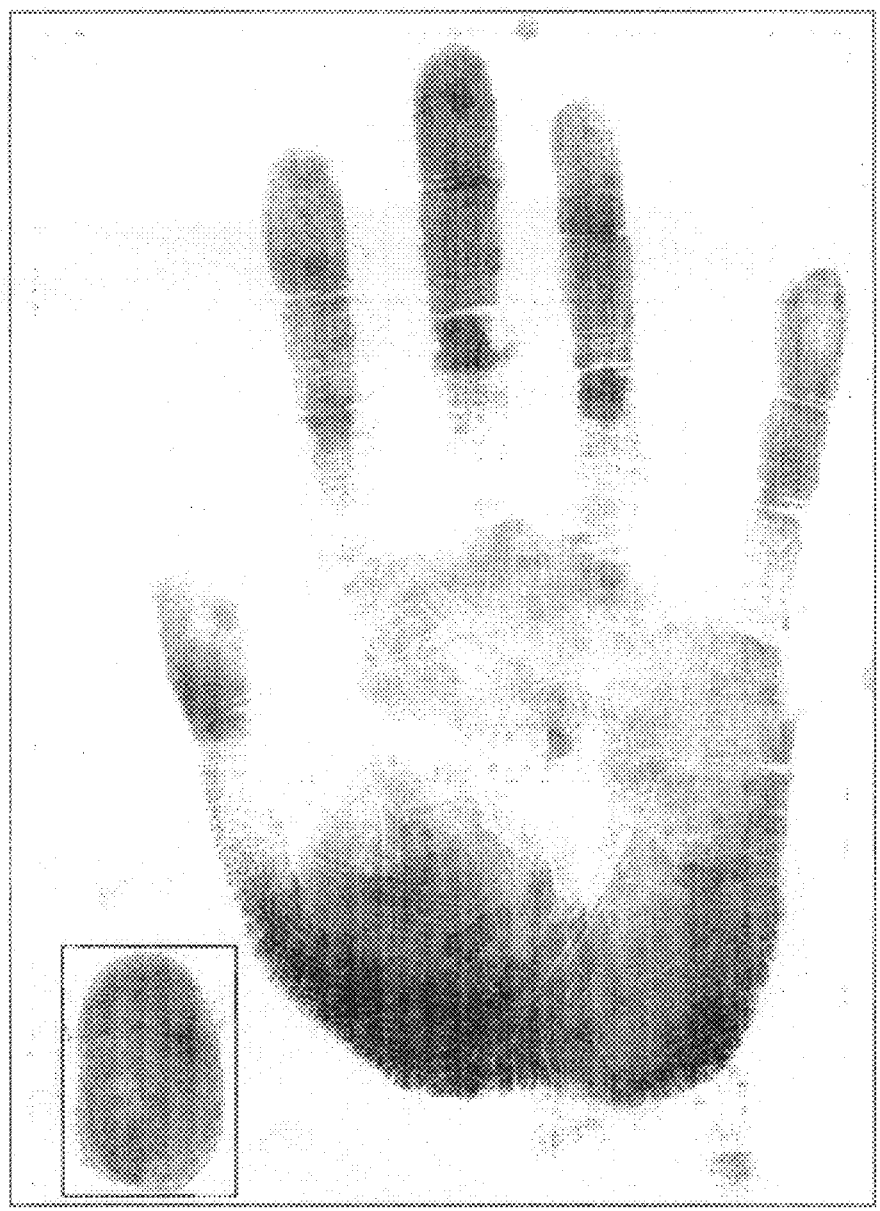
FIG. 2 is an image of palm print which is input into a computer after being stained on an adhesive sheet.

FIG. 2 shows printed images of the palm and thumb of an adult on the adhesive sheet (A5 size) of Example I. After being impressed by the palm, the adhesive sheet was soaked in 1% crystal violet (Sigma, U.S.A.) for 10 sec and then, washed with distilled water to visualize a blue-stained palm print. Thereafter, the adhesive was dried in the air and covered with a transparent plastic film. The blue-stained image was computerized at 300 dpi with the aid of a scanner (Model GT-5000, Epson, Japan). From this file, the palm print image was printed out at the same resolution and shown in FIG. 2.

EXAMPLE III

Magnified Fingerprints

Figure 3:
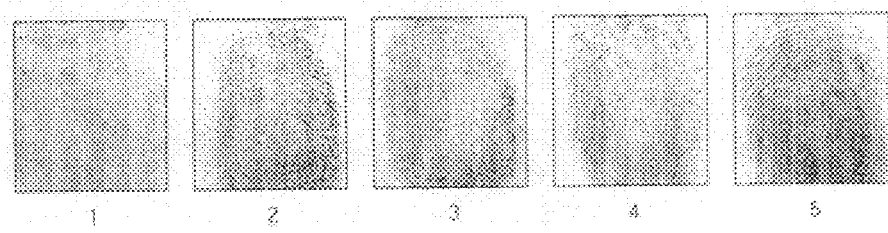
FIG. 3 shows images of the finger prints, magnified from the image of the palm print.

Because the palm print of Example II was recorded in a computer-readable file, an image of the palm print, displayed on a computer monitor, could be magnified to show the fingerprints in detail by use of software, such as Photoshop version 5.0 (Adobe, U.S.A.). If necessary, a digital camera (Ricoh RDC-4300, Japan) equipped with a magnifying lens or close-up lens may be used to magnify only the fingerprint portions and the digital files thus obtained may be directly input into a computer. FIG. 3 shows magnified fingerprint images.

EXAMPLE IV

Optimization of DNA Extraction

DNA was extracted from an adhesive sheet on which a palm print was printed, and amplified by PCR using a profiler system manufactured by Perkin-Elmer. The PCR product was analyzed for DNA profiles, using automatic nucleotide sequencer ABI310 (Perkin-Elmer, U.S.A.).

A piece with a size of 1.5 cm×0.5 cm was cut from the adhesive sheet of Example II and immersed in an extraction buffer which was prepared by mixing 5 µl of protease K (Boehringer Mannheim) with a concentration of 10 mg/ml in 500 µl of a 5% Chelex-100 (Bio-Rad) suspension of mixed ion-exchange resins. After being incubated at 56° C. for 30 min, the solution was heated at 100° C. for 10 min, followed by centrifugation at 13,000 rpm for 10 min. The supernatant was transferred to a new tube and subjected to alcohol precipitation to obtain DNA almost free of inhibitory materials. The DNA, obtained as a dried pellet, was dissolved in 20 µl of TE buffer (10 mM Tris-HCl, pH 8.0, 1 mM EDTA).

FIG. 4 shows multiplex PCR results of 9 STR regions and a part of an amelogenin gene using Profiler-Plus kit (Perkin Elmer). A mixture comprising 20 µl of the DNA solution, 20 µl of a buffer, 10 µl of a pair of primers, and 1 µl of a Taq polymerase (Ampli-Taq Gold, Perkin-Elmer), the latter three being provided from the Profiler-Plus kit, was used in the multiplex PCR. A thermal cycler (T-gradient, Biometra, Germany) was set as follows: 95° C. for 11 min (pre-denaturation); 29 thermal cycles consisting of 95° C. for 1 min (denaturation), 59° C. for 1 min (annealing) and 72° C. for 1 min (elongation); and finally 60° C. for 45 min (post-elongation).

Following the amplification, 3 µl of the sample were added in 15 µl of a molecular weight standard solution prepared by mixing 1 µl of a molecular weight marker labeled with Rox, a different color fluorescent dye provided from the kit, with 24 µl of formamide (Sigma, U.S.A.). The mixture was heated at 95° C. for 3 min, placed on ice for 3 min, and electrophoresed in an automatic nucleotide sequencer (ABI310).

In FIG. 4, a symbol (−) means that a corresponding component or treatment process was omitted in the DNA extraction procedure. The lowest panel resulted from the sample which experienced all of the treatment with the Chelex ion exchange resin, the protease and boiling.

The electropherogram of FIG. 4 was made in such a way that, after the times were measured at which fluorescence-labeled DNA fragments passed a reference point irradiated with a laser beam, the distances from the starting point were calculated backward. The leftmost point in the electropherogram is the reference point. Because heavier DNA fragments moved more slowly, they were positioned at points farther from the reference point. The Profiler-Plus kit had three fluorescent markers different in color. Three STRs in which the fragment size ranges of alleles were not overlapped with one another were subject to one group which was labeled with a fluorescent dye of one color. Thus, nine alleles of STRs appeared in three colors in the electropherogram. Representing the intensity of the fluorescence, the height of the peaks is proportional to the quantity of the DNA used. The peak printed in pale gray at the leftmost position showed amelogenin, and the peaks detected corresponded only to alleles of the X chromosome because the DNA sample used came from a woman.

EXAMPLE V

Additional Removal of Reaction Inhibitory Materials

The results of Example IV indicate that good DNA profiles can be obtained through the treatments with Chelex and proteases and a boiling process. In practice, however, an excess of reaction inhibitory materials is frequently detected according to personal traits, such as skin types and epidermal states upon sampling, so that accurate and clear peaks cannot be read by the procedures described in previous examples.

FIG. 5 shows the difference in DNA profile before and after reaction inhibitory materials are removed. The DNA pellet obtained after the alcohol precipitation of Example IV was dissolved in 100 $\mu$l of TE and then, subjected to spun-column chromatography using Sephadex G-50 with a volume of 1 ml. The DNA solution which passed through the Sephadex tube was dried in vacuum to give a pellet which was subsequently dissolved in 20 $\mu$l of deionized water. PCR was conducted using the Profiler-Plus kit as in Example IV.

EXAMPLE VI

Quantification of DNA Obtained from Adhesive Sheet

In the case obtained from blood, DNA can be quantified by UV absorption or a fluorescent dye such as Hoechst 33258, due to its large amount. In contrast, a trace amount of DNA, as in the case obtained from the epidermis, cannot be directly quantified. An indirect estimation of the quantity of the DNA extracted in Example IV was made by comparing its amplified degree with that of the DNA isolated from blood. In this regard, DNA was obtained from 100 $\mu$l of blood, reacted with Hoechst 33258, and then quantified by the absorbance at 260 nm. The DNA solution was diluted in series to 0.125 ng/$\mu$l. The blood DNA diluted serially or the epidermal DNA extracted from a 1.5 cm×0.5 cm piece of the adhesive sheet was employed as template for PCR, which was conducted under the same condition with the aid of the Profiler-Plus kit (Perkin-Elmer).

The production of a PCR product behaves like the growth of bacteria, forming a sigmoidal curve. In order to carry out quantitative comparison, the production must be in exponential phase. To this end, the PCR was conducted to 29 cycles in this example. For simplification, only the FGA region out of the nine STRs of the Profiler-Plus kit was shown in FIG. 6. The peaks amplified by use of the DNA extracted from a piece (1.5 cm×0.5 cm) of the adhesive sheet showed similar heights to those of the peaks amplified by use of 0.5 ng of blood DNA, which were found to be higher than those obtained from 0.1 ng or 0.25 ng of blood DNA. This result indicates that at least 1 ng of DNA can be obtained from the epidermis in consideration of the presence of reaction inhibitory materials in the adhesive sheet extracts.

EXAMPLE VII

Prevention of the Release of Reaction Inhibitors through Coating

Paper is made through various chemical treatments, and adhesives have complicated compositions. These materials, which compose the adhesive sheet of the present invention, are eluted along with DNA in the course of DNA extraction, deleteriously affecting the PCR of the DNA. To fundamentally eliminate the elution of such potent reaction inhibitors, a non-permeable film is coated on the both sides of the paper in the present invention.

FIG. 7 shows the effect of such coating treatment. The palm was impressed on three different papers: an ordinary sheet of copy paper with no treatment; a paper-based adhesive sheet where only one side of the paper was coated with a film, having an adhesive applied thereon; and a paper-based adhesive sheet where both sides of the paper were coated with a film, having an adhesive applied thereon. The same comparison as in Example IV was made for these three cases. Almost no peaks, except for regularly spaced small peaks (molecular weight markers), were found from the electropherograms for the copy paper and the one-side-coated sheet. This result indicates that the adhesive applied on the adhesive sheet is indispensable for a sufficiently large amount of epidermal samples while the PCR absolutely requires the removal of various compounds released from paper.

EXAMPLE VIII

Multiplex PCR of DNA Extracted from Adhesive Sheet and Its Use in Paternity Tests Real parents and their child impressed their palms on the adhesive sheets of the present invention from which their DNA profiles were constructed using the Profiler-Plus kit commercially available from Perkin-Elmer.

Together with a DNA profile for a standard marker, the DNA profiles are shown in FIG. 8. As seen, the three DNA profiles are different with one another, but the peaks for alleles of each STR region, which are found in the son's DNA profile, are also found at the corresponding positions in either of the parents' DNA profiles, demonstrating Mendelian heredity. In the uppermost graph, the alleles of amelogenin are displayed in a standard ladder form, along with three STR regions.

The result shows that, like the DNA obtained from blood, the DNA extracted from the epidermis by use of the adhesive sheet can be used for kinship identification, including paternity tests.

EXAMPLE IX

Nucleotide Sequencing of Partial ACE Gene and F13A01 STR in DNA Extracted from Adhesive Sheet In the Example, a fragment of the ACE (angiotensinogen converting enzyme) gene, which has only one copy in the whole genome, was subjected to nucleotide sequencing. To this end, two synthetic oligonucleotides, each represented by SEQ ID NO: 1 and NO: 2, were used as primers for the amplification of the ACE gene. For the template of the PCR, 20 µl of the DNA extracted from the adhesive sheet as in Example IV was used while 10 ng of the DNA isolated from blood was used as a control. The PCR consisted of 30 thermal cycles in which heating was conducted in the order of at 94° C. for 1 min, at 58° C. for 1 min and at 72° C. for 1 min.

The PCR products were allowed to undergo the nucleotide sequencing by a terminator cycle sequencing method using Big-Dye Terminator Sequencing kit (Perkin-Elmer). In 10 µl of the amplified DNA template were added 4 µl of Big-Dye Terminator Reaction Mix and 4 µl of a primer (0.8 pmol), which both were provided in the kit, and the resulting reaction solution was added with deionized water to a final volume of 20 µl. This was subjected to 25 thermal cycles in which heating was conducted in the order of at 96° C. for 10 sec, at 50° C. for 5 sec and at 60° C. for 4 min. As recommended in the teaching of the kit, the DNA amplified through the PCR was added at an amount of 30 ng. Electrophoresis was conducted in the ABI310 automatic nucleotide sequencer as in Example IV.

FIGS. 9a and 9b show the nucleotide sequences of a partial ACE gene derived from the blood DNA and the epidermal DNA as templates, respectively. As apparent from figures, the nucleotide sequence of ACE gene extracted from the adhesive sheet was identical to that of the blood DNA.

FIG. 9c shows a nucleotide sequence of the F13A01 STR region, obtained by use of the epidermal DNA extracted from the adhesive sheet. As primers for the amplification of the F13A01 STR gene region, synthetic oligonucleotides described by SEQ ID NO: 3 and NO: 4, were used. In FIG. 9c, nucleotide sequences can be clearly read to the region of base 180. However, two peaks were found to be overlapped from around the region of base 180. This overlapping is attributed to the fact that the genomic DNA isolated from the sample forms a heterozygote at F13A01 STR.

INDUSTRIAL APPLICABILITY

As described above, the DNA isolating method using an adhesive sheet provided by the present invention, is very convenient in DNA sampling and can surmount the problems which are caused by conventional blood sampling methods. Particularly, where palm prints are impressed on the adhesive sheet, the palm prints or fingerprints can be used as a direct identification measure, eliminating the cumbersome photographing and notarizing procedures which until now have otherwise been required when DNA samples for genetic identification are taken from blood or the epithelial cells of the mouth.

Because the adhesive sheet of the present invention is not in a liquid state, it is very easy to store, transport and manage the sample. In addition, it can be delivered via mail. Therefore, the adhesive sheet of the present invention enables a medical examination of the disease-related genes to be simplified without the testee going to a hospital.

The epidermal cells taken on the adhesive sheet are in a dry state, so that the DNA can be stably maintained. Thus, the adhesive sheet is an effective and efficient means for DNA storage for possible reference in the event of incidents, such as plane accidents, kidnap, lawsuits for kinship identification, etc, in addition to allowing the establishment of DNA storage banks.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for obtaining human DNA for genetic analysis, comprising the steps of
   a) taking the epidermis of a testee by means of an adhesive sheet; and
   b) extracting DNA from the epidermis stuck on the adhesive sheet.

2. A method as set forth in claim 1, wherein the epidermis of step a) is the epidermis of the palm, the finger, the foot sole, or the toe.

3. A method as set forth in claim 1, wherein the adhesive sheet comprises a support, one side of which is applied with an adhesive, said support being made of a synthetic resin, fiber, metal, or paper whose both sides are coated with an insoluble film.

4. A method as set forth in claim 1, wherein the step b) is conducted by use of sodium hydroxide solution.

5. A method as set forth in claim 1, wherein the step b) is conducted by immersing a part of or all of the adhesive sheet in an extraction buffer, heating the buffer to 80° C. or higher, precipitating DNA with alcohol, and implementing molecular sieving chromatography.

6. A method as set forth in claim 5, wherein the extraction buffer comprises a mixed ion-exchange resin and a protease.

7. A method for genetic analysis using human DNA, comprising the steps of
   a) taking epidermal scraps from the skin of a testee by use of an adhesive sheet;
   b) visualizing the epidermal print as an image;
   c) recording the image in an optical or electronic medium;
   d) extracting DNA from the epidermal scraps stuck on the adhesive sheet; and
   e) measuring physical or chemical properties of the DNA.

8. A method as set forth in claim 7, wherein the step b) is conducted by staining the adhesive sheet with crystal violet.

9. A method as set forth in claim 7, wherein the step c) employs an analog camera, a digital camera and/or a scanner.

10. A method as set forth in claim 7, wherein the physical or chemical properties of the DNA comprise length of DNA sequence amplified by polymerase chain reaction, hybridization behavior, electrophoretic mobility, and nucleotide sequences.

11. A method as set forth in claim 10, wherein the DNA sequence amplified by polymerase chain reaction comprises one or more short tandem repeat (STR) locus.

12. A method as set forth in claim 7, wherein the step e) employs silver staining, autoradiography or fluorescence labeling.

13. A method for taking epidermis or for storing DNA comprising adhering skin to combined sheets, wherein the combined sheets comprise an adhesive sheet and a protective sheet for protecting an adhesive surface of the adhesive sheet.

14. The method as set forth in claim 13, wherein the adhesive sheet comprises a support whose one side is applied with an adhesive.

15. The method as set forth in claim 14, wherein the support is made of paper, a synthetic resin, fiber, or metal.

16. The method as set forth in claim 14, wherein at least one side of the support is coated with an insoluble film.

17. A kit for taking epidermal scraps or for extracting DNA, comprising crystal violet solution and at least one set of combined sheets comprising an adhesive sheet and a protective sheet for protecting an adhesive surface of the adhesive sheet.

18. A kit as set forth in claim 17, further comprising at least one component selected from the group consisting of mixed ion-exchange resins; proteases and buffer thereof; sodium acetate, potassium acetate or sodium chloride solution; TE buffer or Tris buffer; and users' manual.

19. A kit as set forth in claim 18, further comprising at least one column for molecular sieving chromatography and/or at least one filter.

* * * * *